United States Patent [19]

Charters

[11] Patent Number: 4,724,842
[45] Date of Patent: Feb. 16, 1988

[54] METHOD AND APPARATUS FOR MUSCLE STIMULATION

[76] Inventor: Thomas H. Charters, 9985 S.W. Heather La., Beaverton, Oreg. 97005

[21] Appl. No.: 617,158

[22] Filed: Jun. 6, 1984

Related U.S. Application Data

[63] Continuation of Ser. No. 379,973, May 19, 1982, abandoned.

[51] Int. Cl.⁴ ............................................. A61N 1/00
[52] U.S. Cl. ............................................. 128/423 W
[58] Field of Search ................. 128/363, 364, 423 W, 128/782, 802, 806, 24.1, 25, 25 R; 272/116, 129, 125, DIG. 6; 73/379, 826, 862, 51

[56] References Cited

U.S. PATENT DOCUMENTS

| | | | |
|---|---|---|---|
| 1,344,002 | 6/1920 | Kibler | 272/129 |
| 3,465,592 | 9/1969 | Perrine | 272/DIG. 6 |
| 3,881,496 | 5/1975 | Vredenbregt et al. | 128/423 |
| 3,978,491 | 8/1976 | Lenhart et al. | 128/710 |
| 4,177,819 | 12/1979 | Kofsky et al. | 128/423 R |
| 4,184,678 | 1/1980 | Flavell et al. | 272/129 |

FOREIGN PATENT DOCUMENTS

| | | | |
|---|---|---|---|
| 719635 | 5/1980 | U.S.S.R. | 128/782 |
| 740255 | 6/1980 | U.S.S.R. | 128/423 W |

*Primary Examiner*—Max Hindenburg
*Attorney, Agent, or Firm*—Dellett, Smith-Hill and Bedell

[57] ABSTRACT

An exercise machine or dynamometer is provided with control apparatus for ascertaining the physical position of a patient during an exercise. The patient is then electrically stimulated over selected ranges of motion in order to aid in the exercise.

9 Claims, 7 Drawing Figures

METHOD AND APPARATUS FOR MUSCLE STIMULATION

This application is a continuation of application Ser. No. 379,973, filed May 19, 1982, abandoned.

BACKGROUND OF THE INVENTION

The present invention relates to a muscle stimulation method and apparatus and particularly to a method and apparatus for selectively initiating electrical stimulation in synchronism with certain body movements.

As the result of trauma or surgery, an individual can lose the strength of certain muscles and/or atrophy may occur because of nonuse or confinement in a cast. Physical therapy may be prescribed, including muscle exercise for regaining the lost muscle function. A particular exercise may be defined as isometric wherein the patient exerts force against a fixed object, or isokinetic wherein the patient pushes or pulls against a moving or movable object which has a maximum allowable speed.

In an isokinetic exercise machine known as a dynamometer, a rotatable arm is moved by the patient, wherein the arm is resistive to movement at greater than a preset speed. The patient may exert whatever force he desires at such speed. However, the patient can slow his movement or discontinue movement altogether, e.g. if pain develops, and the machine is constructed for thereupon discontinuing its resistive force. This cessation in resistive force would not occur, for example, if a weight were simply attached to the limb being exercised. Although isokinetic exercise of this type is quite valuable for therapy purposes, nevertheless many patients lack the ability to initiate muscle contraction over either all or part of a normal range of movement, or their ability is so marginal that therapy for muscle restoration is a slow process.

Electrical stimulation can be employed for initiating muscular contraction, especially in patients who have lost motor nerve control. However, electrical stimulation in the past has been employed substantially independently of, rather than in coordination with, mechanical exercise devices. Stimulation has also not been accurately and selectably synchronized with ranges of bodily movement.

SUMMARY OF THE INVENTION

In accordance with the present invention, in a particular embodiment thereof, a rotatable member or arm including means for attachment to the human body, is also provided with angular position detecting means. Control means responsive to the position detecting means actuates an electrical stimulator for supplying electrical stimuli to the human body for assisting the movement defined by the aforementioned arm. The control means can be adjusted, for example, so that electrical stimulation is produced over a given selected range of movement, or in response to extremes of movement. The rotatable member or arm suitably comprises part of an exercise device against which a patient may exert force, or attempt to exert force, in cooperation with electrical stimulation, for apparently bringing about motion of said rotatable member or arm.

The control means suitably comprises first and second comparator circuits for respectively responding to first and second selectable levels of an electrical indication of said angular movement. The control means alternatively comprises differentiating means driving level detecting means which respond to opposite excursion directions of the electrical output proportional to angular movement.

It is accordingly an object of the present invention to provide an improved method and apparatus for electrical stimulation of muscles in coordination with the movement or exercise of said muscles.

It is another object of the present invention to provide an improved method and apparatus of electrical stimulation coordinated with therapeutic isokinetic exercise.

It is another object of the present invention to provide an improved method and apparatus for assisting therapy and restoration of injured or atrophied muscles.

The subject matter which I regard as my invention is particularly pointed out and distinctly claimed in the concluding portion of this specification. The invention, however, both as to organization and method of operation, together with further advantages and objects thereof, may best be understood by reference to the following description taken in connection with the accompanying drawings wherein like reference characters refer to like elements.

DETAILED DESCRIPTION

Figures 1, 2:
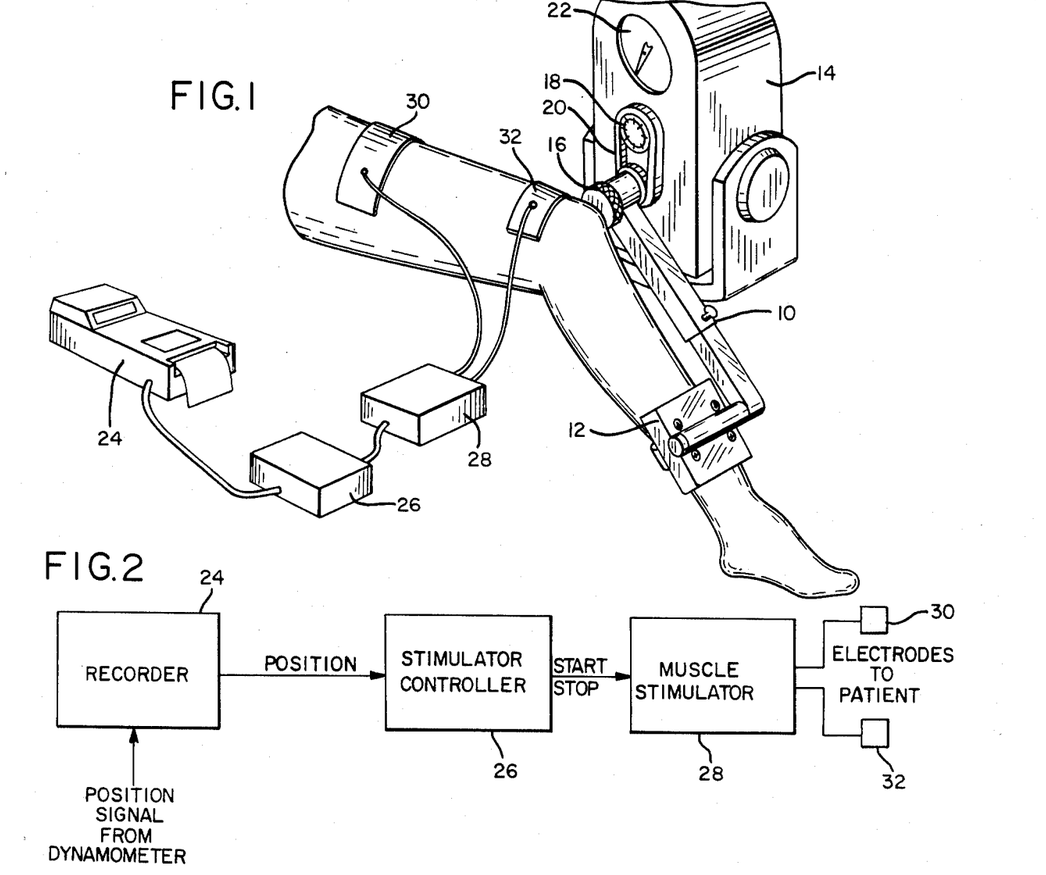
FIG. 1 is a perspective view of a dynamometer for providing isokinetic exercise together with a control system according to the present invention for providing assisting electrical stimulation.
FIG. 2 is a block diagram of the aforementioned system.

Referring to FIG. 1, in the illustrated embodiment, a rotatable member 10 comprises an extensible arm carrying a pad 12 at its lower extremity for attaching to a portion of the human body capable of executing rotational movement, in this case the leg of an individual. The arm 10 is keyed to the input shaft of a "dynamometer" 14 and is held in place on such input shaft by means of a collet 16. The dynamometer is suitably a Cybex II exercise machine, manufactured by Cybex, Ronkonkoma, N.Y. This machine is commonly used by physical therapists and includes a potentiometer 18 driven from the machine's input shaft by way of chain 20. The dynamometer also includes a torque indicator 22 by means of which the exertion of the patient can be measured or observed.

The dynamometer, further described in U.S. Pat. No. 3,465,592 to Perrine, is employed for isokinetic exercise. The device suitably includes a synchronous motor driving a worm which is geared through oppositely rotating clutches to the input shaft. The structure is such that the exercising patient can move no faster than a preset speed (determined by the synchronous motor), but may deliver a measurable torque with respect to the input shaft at the given speed. However, the patient need not exert force against the input shaft nor need he indeed move at all. Thus, the system is superior to systems of weights where continued movement may be required of a patient despite possible pain or injury.

In the described embodiment, an arm position indication, provided by potentiometer 18, is delivered to recorder 24 (via leads not shown in FIG. 1), and a torque indication may be similarly supplied to the recorder. The position information is further delivered to stimulator controller 26 functioning to start and stop operation of muscle stimulator 28, the latter having leads connected to electrodes 30 and 32 making electrical contact with the patient. The muscle stimulator 28 is suitably of the type sold under the trademark "EXER-STIM" by T. H. Charters, Inc., Beaverton, Oreg. The muscle stimulator, when enabled from controller 26, delivers a series of electrical pulsations for contracting desired muscles and assisting the patient in his movements. The muscle stimulator 28 is further disclosed in my U.S. Pat. No. 3,731,111, and is connected as hereinafter more fully described. In the particular embodiment herein disclosed, the stimulator pulse width was 350 microseconds with an amplitude of 95 volts. The pulse frequency is suitably from 17 to 50 Hertz depending upon adjustment.

In the example illustrated in FIG. 1, electrode 30 is suitably located over the rectus femoris muscle or over the vastus lateralis, while electrode 32 is positioned immediately superior to the patella. This placement is suitable for electrical stimulation of the quadriceps muscle group for knee extension, but it is understood correct electrode placement for muscle stimulation in the case of other movements will be understood by the medical practitioner or therapist.

Figure 3:
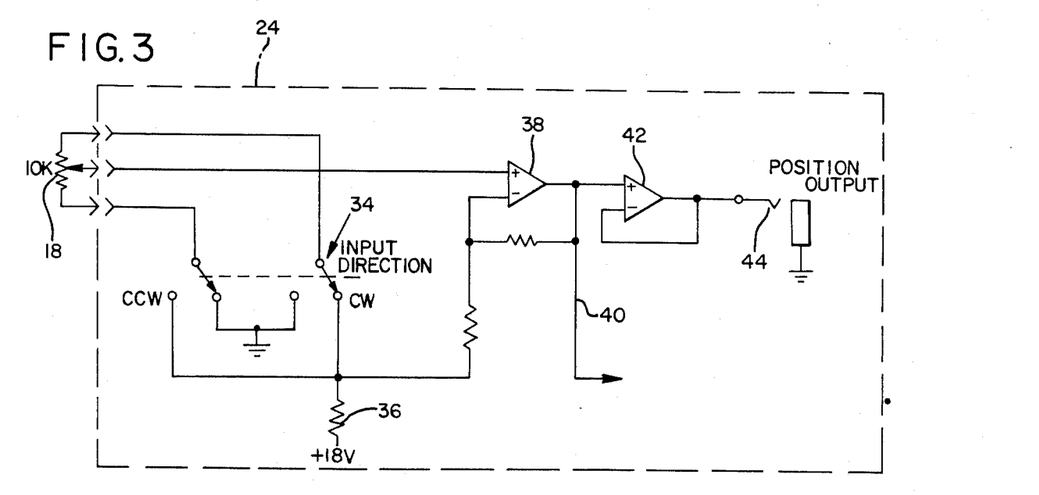
FIG. 3 is a schematic diagram of a portion of a chart recorder, the output of which is employed in the present system.

Turning to FIG. 3, a portion of recorder 24 is illustrated which suitably provides connection between the dynamometer and the stimulator controller 26. The potentiometer 18 from the dynamometer is connected between the movable contacts of a double pole double throw "input direction" switch 34 for changing the relative polarity of the position signal being recorded. By means of this switch, a selected end of the potentiometer is connected to a positive 18 volts via resistor 36, and the other end is grounded. The movable tap of potentiometer 18 is coupled through operational amplifier 38 to output lead 40 which suitably supplies the position signal from the potentiometer to recording pen circuits (not shown). The output of amplifier 38 is also coupled via unity gain isolating amplifier 42 to position output jack 44 adapted for connection via a suitable cable to stimulator controller 26.

Figure 4:
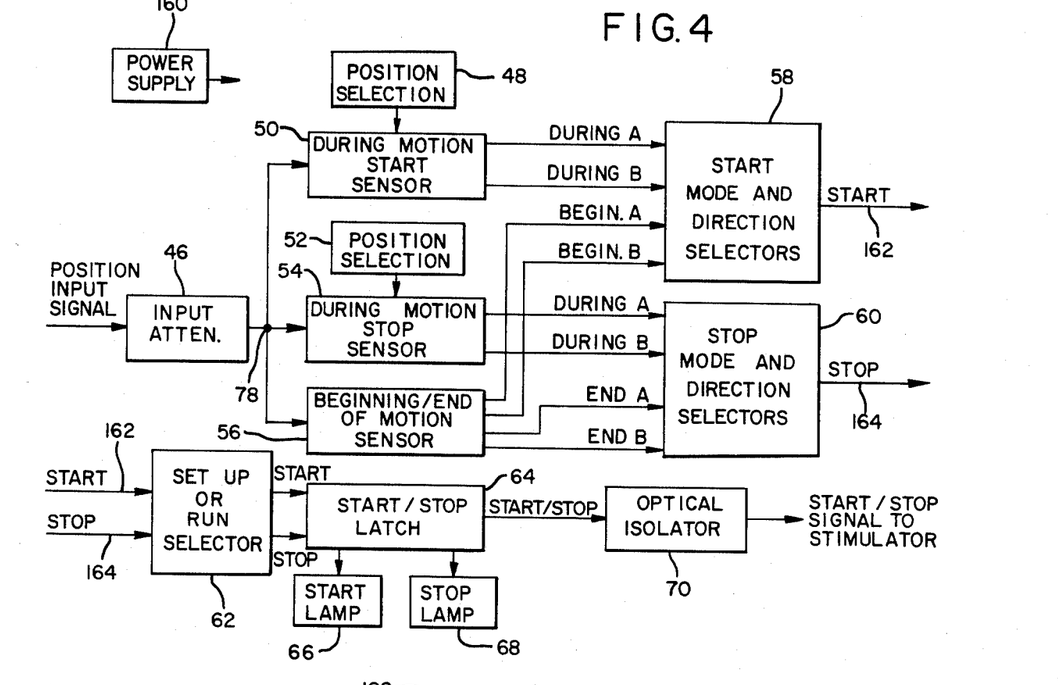
FIG. 4 is a block diagram of a stimulator controller portion of the system according to the present invention.

The stimulator controller 26 is illustrated in block diagram form in FIG. 4. The stimulator controller is adapted to select the points during the exercise movement of the patient at which electrical stimulation is initiated and at which electrical stimulation is concluded. Thus, it may be desired that electrical stimulation be applied during a portion of the extension movement of the patient's leg, or it may be desired that electrical stimulation be applied whenever the patient endeavors to move his leg in a certain direction, e.g. in extension.

Referring to FIG. 4, the position signal from the dynamometer potentiometer, via recorder 24, is applied to common terminal 78 by way of input attenuator 46.

Common terminal 78 provides the position signal to during-motion-start sensor 50, to during-motion-stop sensor 54 and to beginning/end-of-motion sensor 56. A position selection device 48 comprising a potentiometer selects a point in the range of movement of the patient at which it may be desired to start electrical stimulation, and this position selection is applied to during-motion-start sensor 50. Similarly, position selection device 52 which comprises a potentiometer is utilized to select the point in the patient's range of movement at which electrical stimulation is to be completed, and this selection is supplied to during-motion-stop sensor 54. Reversed polarity outputs from sensor 50 are coupled to the start mode and direction selectors 58, and are designated "during A" and "during B", wherein "A" and "B" refer to opposite directions of limb movement. Similarly designated outputs of sensor 54 are applied to stop mode and direction selectors 60. As will hereinafter be more fully described, the selectors 58 provide a start signal at lead 162 when the desired patient position is reached (at which electrical stimulation is to be initiated), after which selectors 60 supply an output on lead 164 when a second patient position is reached (at which electrical stimulation is to be concluded).

Leads 162 and 164 are connected to "set up or run selector" 62 which controls start/stop latch 64. A start indication on lead 162 in general sets latch 64 in a given state, while a stop indication on lead 164 resets the latch. Latch 64 provides indicating outputs to start and stop lamps 66 and 68 respectively, and also provides a start/stop output to optical isolator 70 for controlling the muscle stimulator 28.

Power supply 160 suitably receives line power and provides appropriate DC voltages to the various circuits. However, it will be noted this power supply is isolated from the muscle stimulator by optical isolator 70.

Instead of starting electrical stimulation at a given point "during motion" and stopping stimulation at a second point "during motion", it may be desired to initiate stimulation with the beginning of motion in a particular direction and stop stimulation at the end of motion. "Beginning" and "end-of-motion" options are useful where starting or stopping is desired near the limits of movement where the patient might not always move quite far enough to pass through a particular position. Beginning/end-of-motion sensor 56 detects beginning and end conditions and provides alternative controls for the latch 64 which can be selected by the selectors 58 and 60. Sensor 56 differentiates the position signal to detect the polarity and magnitude of its slope. Then, four comparators (as hereinafter more fully described) produce positive output steps, one at a time, when the input indicates the following:

1. Beginning-of-motion in one direction.
2. End-of-motion in that direction.
3. Beginning-of-motion in the opposite direction.
4. End-of-motion in the opposite direction.

Over all choices for starting the stimulator (by selection with selector 58 and potentiometer 48) are then:

1. "During motion" at a particular position, moving in either direction, and
2. At the "beginning-of-motion" in either direction.

And over all choices for stopping the stimulator (by selection with selector 60 and potentiometer 52) are then:

1. "During motion" at a particular position, moving in either direction, and

2. At the "end-of-motion" in either direction.

Figure 5:
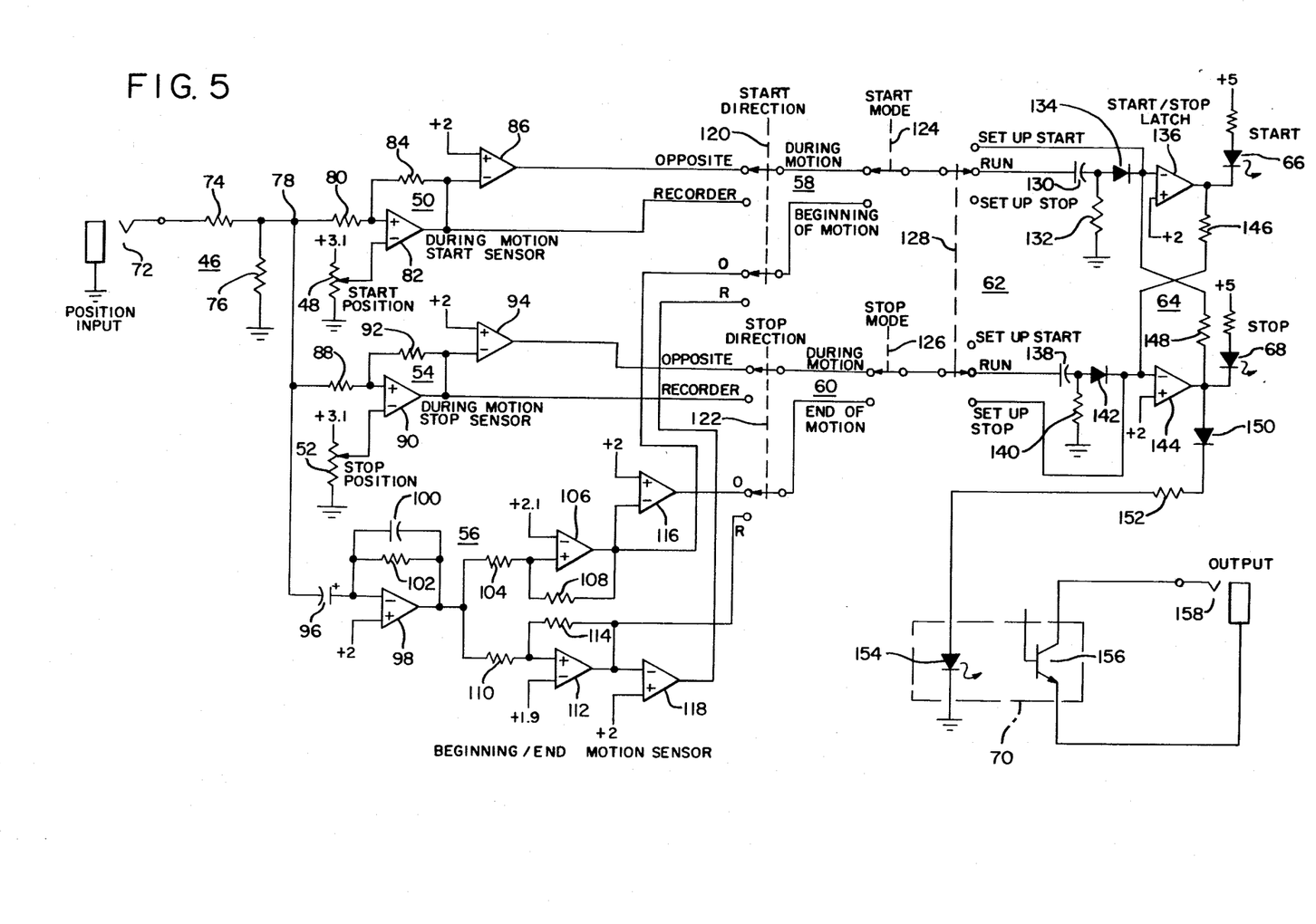
FIG. 5 is a schematic diagram of the FIG. 4 controller.

Considering the stimulator controller 26 in greater detail, reference is made to FIG. 5. Input jack 72 receives the position output via recorder 24 and this position signal is coupled through attenuator 46, comprising resistors 74 and 76, to common input terminal 78. The input to the attenuator varies from 0 volts to 8.37 volts representing 300° of arm movement for the dynamometer. This signal is attenuated to the range of 0 volts to 3 volts. A resistor 80 connects terminal 78 to one input of comparison amplifier 82 comprising part of sensor 50, wherein potentiometer 48 supplies an opposite polarity input. When the input signal at terminal 78 exceeds a predetermined value, as set by potentiometer 48, amplifier 82 supplies a positive going output, and is aided in providing a rapid switching transition by positive feedback resistor 84. The output of amplifier 82 is supplied to a terminal marked "recorder" of the start direction switch 120, while inverter 86 interposed between the output of amplifier 82 and "opposite" terminal of switch 120 provides a positive going indication when the input signal at terminal 78 falls below the value selected with potentiometer 48. The designations "recorder" and "opposite" correspond to the "during A" and "during B" designations of FIG. 4. That is, if it is desired electrical stimulation begin when the position signal exceeds a given value for a relatively positive going excursion of recorded movement, then the switch 120 is positioned to select the terminal marked "recorder". If, on the other hand, it is desired to start electrical stimulation when the movement depicted on the recorder falls below a given selected value, then the "opposite" terminal is selected by the switch. The "recorder" designation merely refers to a convention selected in the recorder for noting the "positive" direction of body movement.

The sensor 54 operates in a similar manner, with common terminal 78 being coupled via resistor 88 to the positive terminal of comparison amplifier 90 having its negative input terminal connected to potentiometer 52. Amplifier 90 is provided positive feedback with resistor 92 and quickly changes states when the input exceeds the value selected by the potentiometer. The output of amplifier 90 is connected to the terminal of stop direction switch 122 marked "recorder", while the output of amplifier 90 is inverted by inverter amplifier 94 to provide the "opposite" input to stop direction switch 122.

The values selected by potentiometers 48 and 52 will then be effective in determining the points "during motion" at which stimulation is to be initiated and stopped. This assumes start mode switch 124 and stop mode switch 126 are in the "during motion" positions. If switches 124 and 126 are in the beginning-of-motion and end-of-motion positions respectively, then the beginning/end-of-motion sensor 56 will control operation of latch 64 and therefore the muscle stimulator.

The beginning/end-of-motion sensor 56 comprises a differentiating circuit including a capacitor 96 interposed between terminal 78 and an input terminal of a first comparator comprising operational amplifier 98 having a negative feedback circuit consisting of capacitor 100 in parallel with resistor 102. A reference of plus two volts is applied to the non-inverting input of amplifier 98. The output of amplifier 98 is coupled through resistor 104 to an input terminal of comparator amplifier 106 having resistor 108 disposed in positive feedback relation. The output of amplifier 98 is also supplied via resistor 110 to comparator amplifier 112 having resistor 114 disposed in positive feedback relation.

When the input position signal reaches a negative extremity and starts upwardly (indicating a beginning of motion for the patient), the amplifier 98 will deliver a negative going step which will exceed (be less than) the positive 1.9 volt reference input of comparator amplifier 112, delivering an output, which via inverter 118, will be appropriate for an "R" (recorder) input of ganged start direction switch 120. At the end of the positive going input signal, the output of amplifier 98 will rise and produce a positive going signal at the output of amplifier 112 which is appropriate for the "R" (recorder) input of ganged stop direction switch 122.

The outputs of beginning/end-of-motion sensor 56 substitute for the outputs of sensors 50 and 54 assuming switches 124 and 126 are moved from the "during motion" position to the beginning-of-motion and end-of-motion positions respectively. The "R" or recorder designation for the outputs of amplifiers 112 and 118 is in keeping with the convention of recorder tracings. For the opposite, or "0" type of operation, switches 120 and 122 are shifted to their opposite terminals. The output of amplifier 98 will cause the output of comparator amplifier 106 to change when the input position signal has reached its highest value and is starting to decrease. The resulting positive going signal at the output of amplifier 98 will exceed the reference 2.1 volts applied to comparator amplifier 106, with the output of amplifier 106 being coupled to the "0" (opposite) input of start direction switch 120. At the end of downward movement, the output of amplifier 98 will drop, causing a rise in the output of amplifier 116 whereby the end of motion is detected. The beginning and end of motion options are particularly useful when starting or stopping of stimulation is desired near the limits of movement where the patient might not always move quite far enough to pass through a particular position. Thus, the reference input voltage applied to the comparator amplifier 112 establishes a threshold value for starting and stopping stimulation when the switches 120, 122 select their "recorder" inputs, and the reference input voltage applied to the comparator amplifier 106 establishes a threshold value for starting and stopping stimulation when the switches 120, 122 select their "opposite" inputs.

Any mix of start and stop operations is possible. Thus, switch 124 may be set to start stimulation "during motion" and switch 126 may be set to stop operation at the "end-of-motion".

The set-up-start function allows the start signal, only, to control the start/stop output. In this way attention can be focused on start conditions, only, since stop signals are not coupled. Likewise the set-up-stop function allows the stop signal, only, to control the start/stop output. In the run function the start signal and the stop signal each cause starting and stopping of latch 64. Thus, in the set-up-start position, switch 128 delivers the signal selected by start mode switch 124, and latch 64 will continue in an on or set condition so long as a start signal continues to be generated. If, on the other hand, switch 128 is in the set-up-stop position, only the output selected by switch 126 will control latch 64, causing the same to be reset for the duration of the stop input.

When switch 128 is in the run position, the start signal from switch 124 is coupled via capacitor 130 to the anode of diode 134 connected to the inverting input of amplifier 136, while resistor 132 returns the capacitor to ground. Capacitor 130 and resistor 132 perform a differentiating function, and diode 134 allows only positive spikes to set the latch. Similarly, a capacitor 138 couples the stop signal to the anode of diode 142, the cathode of which is coupled to the inverting input of amplifier 144, while capacitor is returned to ground through resistor 140. Components 138 and 140 form a differentiator and diode 142 passes only positive spikes such that the latch can be reset in response to stop signals. Latch 64 is a bistable multivibrator, cross-coupled in conventional manner by means of resistors 146 and 148. The latch "remembers" its last instruction (start or stop) until it receives the opposite instruction. The set up functions bypass the capacitive coupling and allow the start and stop levels instead of steps to control the state of the latch.

The outputs of amplifiers 136 and 144 are connected respectively to light emitting diodes 66 and 68 which indicate the on and off or start and stop conditions of the latch and therefore of the muscle stimulator driven by the latch. The output of amplifier 144 is coupled by means of diode 150 in series with resistor 152 to a light emitting diode 154 forming part of an optical isolator 70 further including light operated transistor 156. Transistor 156 forms a switch the terminals of which are accessible via jack 158, and this switching transistor may in effect be substituted for the battery switch as described in my aforementioned patent for energizing the muscle stimulator to provide a series of stimulation pulses to the patient. Since an optical isolator is utilized, the patient is protected from electrical shock from an outside source inasmuch as no path to ground exists through the patient and the stimulator controller.

Figure 6:
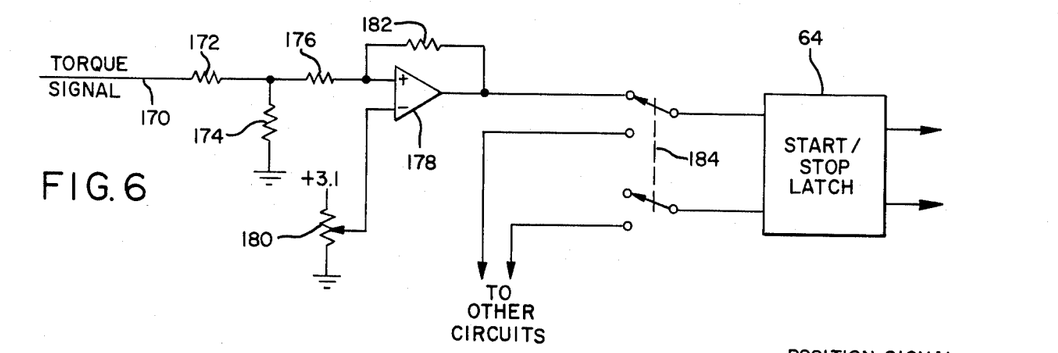
FIG. 6 is a schematic diagram of an alternative system for providing electrical stimulation in response to torque.

Referring to FIG. 6, a circuit is illustrated for providing the initiation of electrical stimulation in response to torque. For isometric exercise (as opposed to isokinetic exercise) wherein muscles are contracted without movement of the limb, the dynamometer arm is locked at a desired position and the patient pushes against it. The dynamometer provides an electrical torque output (not shown) for the recorder 24, and is employed as an electrical input on lead 170 in FIG. 6. The signal on lead 170 is attenuated by resistors 172 and 174, with the center tap therebetween being coupled to the non-inverting input of comparison amplifier 178 via resistor 176. The amplifier 178 also receives a comparison input from potentiometer 180 which is employed for setting a desired level of torque at which it is desired electrical stimulation will begin. Amplifier 178 is provided with positive feedback resistor 182 so as to deliver a rapid switching output when the preset torque is exceeded. The output of amplifier 178 is suitably connected to the start stop latch 64 by means of a switch 184 (not shown in the prior drawings). The output of switch 184 may be connected, for example, to the set-up-start input of the latch, with switch 184 selecting between the circuit of FIG. 6 and the set-up-start and set-up-stop inputs of FIG. 5.

Figure 7:
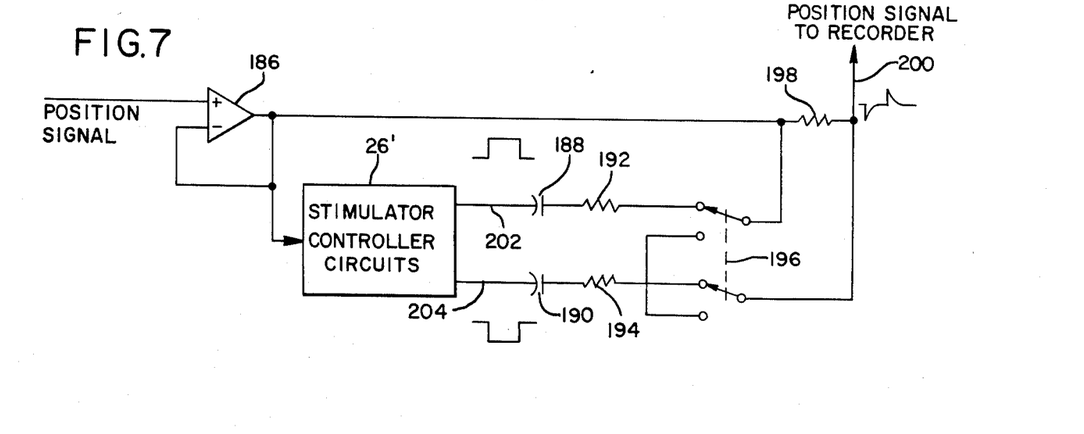
FIG. 7 is a schematic diagram of circuitry for providing stimulation indications for the aforementioned recorder.

FIG. 7 illustrates a circuit for placing markers on the chart of recorder 24 when the start and stop signals occur. For using this circuit, the connection between the dynamometer and the recorder is interrupted, and the position signal from the dynamometer potentiometer is provided as an input to buffer amplifier 186. The output of amplifier 186 is then connected to the stimulator controller circuits 26' in place of the position input signal ordinarily applied to input attenuator 46 as illustrated in FIGS. 4 and 5. It is understood the stimulator controller circuits 26' otherwise correspond to the circuitry described in FIGS. 4 and 5, with leads 202 and 204 comprising output leads from amplifiers 136 and 144 respectively. These outputs are coupled through capacitors 188 and 190 in series with resistors 192 and 194 respectively and in series with the contacts of selection switch 196 whereby a differentiated version of the output of latch 64 is placed across resistor 198 connected in series with the output of amplifier 186. Lead 200 is then connected to the recording pen circuits of the recorder. Approximately equal amounts of charge are injected into and received from each end of resistor 198, and any unbalanced charge is absorbed by the low output impedance of amplifier 186. In this way, the position signal at a controller 26' is left undisturbed, but the position signal to the recorder has markers added thereto, e.g. for the recording of patient position versus time, for indicating the start and stop of stimulation. In the second position of switch 196, the resistor 198 is disconnected from the differentiating circuits to eliminate the markers on the waveform chart.

Since the stimulator circuit according to the present invention is adapted to provide electrical stimulation signals in response to physical position of the patient, e.g. during limb movement, it is able to assist and promote muscle function, particularly for ranges of muscle function not otherwise easily attained by the patient. For example, in a patient recovering from trauma or surgery, the ability to contract affected muscles is reduced, sometimes dramatically. The electrical stimulation helps the muscles to contract and recover strength for given ranges of movement. Even in a healthy, uninjured person, electrical stimulation plus simultaneous voluntary effort can produce thirty percent more torque than with voluntary effort alone. Thus, the electrical stimulus to the muscles and nerves of the patient augments voluntary muscle contraction, and the stimulator controller can be employed to start and stop the stimulator at any desired positions of the exercising limb. The synchronized muscle stimulation is able to build strength faster through the recruitment of more muscle fibers than could be recruited by voluntary effort alone.

In addition to facilitating restoration of muscles to normal strength and normal size, the electrical stimulation synchronized with limb movement can produce other desirable effects. Returning to the example of FIG. 1, for individuals who have patello-femoral-syndrome wherein the patella doesn't track in the groove in the femur, electrical stimulation can enable otherwise impossible leg extension by contracting the vastus medialis to properly move the knee cap. Leg movement can also be enabled despite chondromalacia, or a rough surface on the underside of the kneecap. This condition may exaggerate the patello-femoral problem, but may be separate, and by strengthening contraction of the vastus medialis, the exercise can be facilitated. Eventually, the vastus medialis, as well as other muscles involved, can be strengthened as the result of stimulation and exercise so as to function in a normal manner, this of course being the function of the exercise and stimulation program.

Furthermore, electrical stimulation is known to reduce pain by direct stimulation of the peripheral sensory nerves. Thus, exercises may be enabled which may be at least initially painful to the patient.

Although electrical stimulation in respect to leg extension exercise has been described by way of example, it is understood the invention is applicable to many other movements and exercises. One of the electrodes is suitably placed over the "motor points" for the muscles to be exercised and the other electrode can be placed anywhere that additional muscle response is desired, or at a neutral point away from large muscles. In the example, the electrode 30 is illustrated in position for stimulating the rectus femoris and electrode 32 is positioned for stimulating the vastus medialis.

While I have shown and described a preferred embodiment of my invention, it will be apparent to those skilled in the art that many changes and modifications may be made without departing from my invention in its broader aspects. I therefore intend the appended claims to cover all such changes and modifications as fall within the true spirit and scope of my invention.

I claim:

1. The method of providing stimulation to promote muscle exercise in a human patient, comprising:

moving of a human patient's body portion in conjunction with a dynamometer arm to which said body portion is attached for providing isokinetic exercise as the human patient exerts against the dynamometer arm, detecting an interval of substantially continuous movement of said body portion corresponding to the condition of bodily motion between when movement of the body portion is started and when movement of said body portion is concluded regardless of the specific positions involved, and in response to said detection electrically stimulating said body portion over said interval.

2. Apparatus for stimulating muscle exercise comprising:

a rotatable member having a predetermined axis of rotation and including means for attaching said rotatable member to a selected portion of the human body for simultaneous rotational movement, angular position detecting means coupled to said rotatable member for indicating the angular position of said rotatable member about said axis of rotation, an electrical stimulator adapted to provide electrical output signals, said electrical stimulator having electrodes energized therefrom for placement in contact with the human body proximate said selected portion for transmitting said electrical signals to said selected body portion, and control means responsive to said angular position detecting means for actuating said electrical stimulator to provide said electrical output signals over a selected range of angular positions of said rotatable member between a selected first angular position and a selected second angular position different from said first angular position, whereby to stimulate contraction of muscles in said body portion and assist the angular movement of said body portion between said angular positions, wherein said first angular position selectively corresponds to a detected beginning-of-motion angular position for said rotatable member and said second angular position selectively corresponds to a detected end-of-motion angular position for said rotatable member, and wherein said angular position detecting means provides an electrical output indication substantially proportional to angular movement and said control means comprises differentiating means and level detecting means driven by said differentiating means for responding to the excursion direction of said electrical output indication for starting and stopping said electrical stimulator.

3. The apparatus according to claim 2 wherein said differentiating means comprises a differentiating amplifier and said level detecting means comprises at least one comparator circuit having a comparison level different from the normal operating level of said differentiating amplifier.

4. Apparatus for stimulating exercise comprising:

a rotatable member having a predetermined axis of rotation and including means for attaching said rotatable member to a selected portion of the human body for simultaneous rotational movement, angular position detecting means coupled to said rotatable member for indicating the angular position of said rotatable member about said axis of rotation, an electrical stimulator adapted to provide electrical output signals, said electrical stimulator having electrodes energized therefrom for placement in contact with the human body proximate said selected portion for transmitting said electrical signals to said selected body portion, and control means responsive to said angular position detcting means for actuating said electrical stimulator to provide said electrical output signals over a selected range of angular positions of said rotatable member between a selected first angular position and a selected second angular position different from said first angular position, whereby to stimulate contraction of muscles in said body portion and assist the angular movement of said body portion between said angular positions, wherein said angular position detecting means provides an electrical output indication substantially proportional to angular movement and said control means comprises first and second comparator circuits for respectively responding to first and second selectable levels of said electrical output indication for detecting said first and second angular positions for respectively providing outputs suitable for starting and stopping said electrical stimulator, said control means further comprising differentiating means driving first and second level detecting means for responding to first and second excursion directions of said electrical output indication for providing outputs suitable for starting and stopping said electrical stimulator, and switching means receiving said respective outputs for selectively starting and/or stopping said electrical stimulator in response to said comparator circuits or said level detecting means.

5. The apparatus according to claim 4 wherein said detcting means provides separate outputs according to the rotational direction of the rotatable member, said apparatus further including switching means for selecting between the polarities of outputs generated by said control means for selecting the dirction of the rotatable member for which said starting and stopping of said stimulator is accomplished.

6. Apparatus for stimulating muscle exercise comprising:
- a rotatable member having a predetermined axis of rotation and including means for attaching said rotatable member to a selected portion of the human body for simultaneous rotational movement,
- angular position detecting means coupled to said rotatable member for responding to the angular position of said rotatable member about said axis of rotation,
- an electrical stimulator adapted to provide electrical output signals, said electrical stimulator having electrodes energized therefrom for placement in contact with the human body proximate said selected portion for transmitting said electrical signals to said selected body portion,
- and control means responsive to said position detecting means for detecting a change in the status of said position detecting means between detection of a condition of motion and detection of a condition of non-motion, regardless of the specific angular position at which the change occurs, and in response thereto changing the operational status of said electrical stimulator between one of providing electrical stimulation and one of providing no electrical stimulation.

7. The apparatus according to claim 6 wherein said rotatable member comprises part of an exercise device against which an individual exerts force to produce said rotational movement, said rotatable member resisting angular movement in exercising said portion of the body.

8. The apparatus according to claim 6 wherein said control means is responsive to said position detecting means for detecting when motion starts and detecting when motion stops, for causing said electrical stimulator to provide said electrical output signals as long as motion continues, and for causing said electrical stimulator to discontinue said electrical output signals when said motion stops.

9. Apparatus for stimulating muscle exercise comprising:
- a rotatable member having a predetermined axis of rotation and including means for attaching said rotatable member to a selected portion of the human body for simultaneous rotational movement,
- an electrical stimulator adapted to provide electrical output signals, said electrical stimulator having electrodes energized therefrom for placement in contact with the human body proximate said selected portion for transmitting said electrical signals to said selected body portion,
- and control means including means responsive to rotation of said rotatable member and for detecting velocity of said rotatable member for changing the operational status of said electrical stimulator between one of providing no electrical stimulation and one of providing electrical stimulation in response to the velocity of said rotatable member exceeding a predetermined threshold value.

* * * * *

UNITED STATES PATENT AND TRADEMARK OFFICE
CERTIFICATE OF CORRECTION

PATENT NO. : 4,724,842
DATED      : February 16, 1988
INVENTOR(S) : THOMAS H. CHARTERS It is certified that error appears in the above-identified patent and that said Letters Patent is hereby corrected as shown below:

Column 10, line 15, after "stimulating" insert --muscle--.

Column 10, line 32, "detcting" should be --detecting--.

Column 10, line 62, "detcting" should be --detecting--.

Column 11, line 13, "outpout" should be --output--.

Signed and Sealed this

Twentieth Day of December, 1988

Attest:

DONALD J. QUIGG

*Attesting Officer*   Commissioner of Patents and Trademarks